United States Patent [19]

Froix

[11] Patent Number: 5,607,467
[45] Date of Patent: Mar. 4, 1997

[54] EXPANDABLE POLYMERIC STENT WITH MEMORY AND DELIVERY APPARATUS AND METHOD

[76] Inventor: Michael Froix, 3433 Woodstock La., Mountain View, Calif. 94040

[21] Appl. No.: 516,091

[22] Filed: Jun. 23, 1993

Related U.S. Application Data

[63] Continuation of Ser. No. 874,181, Apr. 24, 1992, abandoned, which is a continuation of Ser. No. 582,531, Sep. 14, 1990, Pat. No. 5,163,952.

[51] Int. Cl.$^6$ .............................. A61F 2/06; A61M 29/00
[52] U.S. Cl. ................... 623/1; 623/12; 606/195
[58] Field of Search ................... 623/1, 11, 12; 606/191, 194, 195, 198; 600/36

[56] References Cited

U.S. PATENT DOCUMENTS

| | | | |
|---|---|---|---|
| 4,904,272 | 2/1990 | Middleton et al. | 623/66 |
| 5,163,952 | 11/1992 | Froix | 623/1 |
| 5,258,020 | 11/1993 | Froix | 623/1 |

FOREIGN PATENT DOCUMENTS

| | | |
|---|---|---|
| 2035350 | 6/1980 | United Kingdom . |
| 2120946 | 12/1983 | United Kingdom . |
| 2139898 | 11/1984 | United Kingdom . |

OTHER PUBLICATIONS

Radionics, Inc., Neurosurgical Instruments, catalog sheet for Trigeminal Neuralgia Kit, 1981.

*Primary Examiner*—Debra S. Brittingham
*Attorney, Agent, or Firm*—Flehr, Hohbach, Test, Albritton & Herbert

[57] ABSTRACT

Self-restrained stent for use in a lumen of a vessel of a patient having a body with the vessel therein, comprising a substantially cylindrical member formed of a plastic material having a built-in elastic predetermined diameter and having a memory provided therein of a diameter greater than the predetermined diameter. The plastic is characterized in that it will attempt to assume the greater diameter in its memory upon occurrence of one or more of the following conditions:

(a) adsorption of heat by the plastic material;
(b) adsorption of a liquid by the plastic material; and
(c) a change in the pH in the liquid in which the plastic member is disposed.

10 Claims, 1 Drawing Sheet

EXPANDABLE POLYMERIC STENT WITH MEMORY AND DELIVERY APPARATUS AND METHOD

This is a continuation of application Ser. No. 07/874,181 filed Apr. 24, 1992, abandoned, which is a continuation of application Ser. No. 07/582,531 filed Sep. 14, 1990, now U.S. Pat. No. 5,163,952.

This invention relates to an expandable polymeric stent with built-in elastic memory and delivery apparatus and method for use therewith.

Many different types of stents have heretofore been provided. For example, stents have been provided to attempt to prevent post-angioplasty vessel reclosure. Typically, such intravascular stents have been utilized in the region of the stenosis to maintain the passageway through the stenosis. Such stents usually have been formed of metal. Such metal stents have been found to be intrinsically thrombogenic because of their net surface charge and surface irregularities. In addition, expandable metal stents have created vessel wall thinning as well as intimal hyperplasia within the stent and at the borders of the stent. These can be caused by uneven circumferential contact of the stent with the vessel endoluminal surface, compliance mismatch between the stent and the vessel wall and excessive stent stiffness. A stent formed of plastic is disclosed in U.S. Pat. No. 4,820,298. As disclosed therein, a thermoplastic polyester polycarbonate copolymer is formed into a helical coil by providing a linear extrusion and winding the same on a mandril and reheating to form a helical spring coil. Strand material is secured to the helical coil. The stent is inserted with a stylet. When the stylet is removed, the stent expands under its recovery memory to assume a helical configuration. This recovery memory is based upon the fact that it was formed from a linear strip and wound onto a mandril which resulted in stored energy, causing it to expand into a helix when released from the stylet. The adjacent loops of the helical stent are constrained by the strand material which has been secured thereto. It is believed that even though such a stent is formed of plastic, it has a number of disadvantages making it unsuitable for use in many applications. It is necessary to mechanically restrain the stent to prevent it from expanding prior to insertion into the vessel. Also it is believed that it is hard to predict the expansion forces exerted when it is released. There is therefore a need for an improved stent.

In general it is an object of the present invention to provide a plastic stent which has a built-in elastic memory, a delivery apparatus and method for use with the same.

Another object of the invention is to provide a stent of the above character which is self-restrained permitting it to be readily inserted into a vessel of a patient.

Another object of the invention is to provide a stent of the above character which has low protein adsorption and is biocompatible.

Another object of the invention is to provide a stent of the above character which need not be physically constrained from expansion prior to placement in the vessel of a patient.

Another object of the invention is to provide a stent of the above character which can be provided with a predetermined stiffness to match the compliance of the vessel.

Another object of the invention is to provide a stent of the above character which can be provided with a surface which facilitates intimal and endothelial cell growth to enhance the biocompatibility of the stent.

Another object of the invention is to provide a stent of the above character which can carry medical agents such as thrombolytic agents, growth factors, and slow release medications.

Another object of the invention is to provide a stent of the above character which will expand to a greater diameter upon being subjected to an external factor.

Another object of the invention is to provide a stent of the above character which has a thermal transition incorporated therein.

Another object of the invention is to provide a stent of the above character which has been crosslinked.

Another object of the invention is to provide a stent of the above character which can be readily and economically manufactured.

Another object of the invention is to provide a stent of the above character which can be readily positioned in the desired location in the vessel of the patient.

Additional objects and features of the invention will appear from the following description in which the preferred embodiments are set forth in conjunction with the accompanying drawings.

In general, the stent of the present invention is for use in the lumen of a vessel of a patient having a body with the vessel therein. The stent is comprised of substantially a cylindrical member formed of a plastic material. The stent has a predetermined diameter and has a memory provided therein of a diameter greater than the predetermined diameter. The plastic is characterized in that it will attempt to assume the greater diameter in its memory upon occurrence of one or more of the following conditions:

(a) adsorption of heat by the plastic;

(b) adsorption of liquid by the plastic; and (c) a change in pH in the liquid in contact with the plastic.

In the delivery apparatus and method, a balloon catheter is utilized for delivering the stent to the desired site. When the balloon with the stent thereon has been delivered to the desired site, the balloon can be inflated to help expand the stent when the stent is subjected to certain factors and conditions. Thereafter the balloon is deflated and the balloon catheter is removed leaving the stent in place. The stent is caused to assume the greater diameter of its memory by the adsorption of heat by the plastic, the adsorption of liquid by the plastic, or a change in the pH in the liquid surrounding the plastic.

Figure 1:
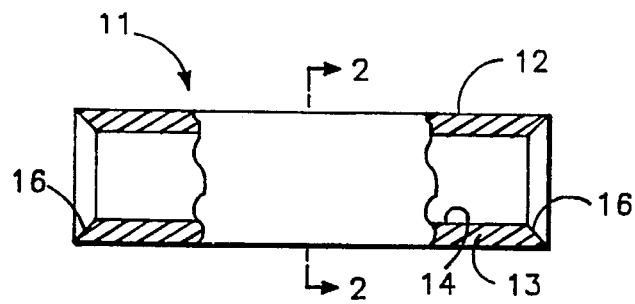
FIG. 1 is a side elevational view partially in cross section of a stent incorporating the present invention.
Figure 2:
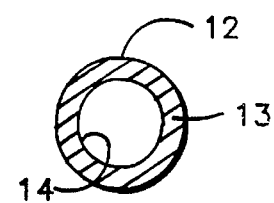
FIG. 2 is cross sectional view taken along the line 2—2 of FIG. 1.

As more particularly shown in the drawings, the stent 11 as shown in FIGS. 1 and 2 is in the form of a generally cylindrical tubular member 12 made of plastic. It is provided with a cylindrical wall 13 which forms a flow passage or lumen 14 extending therethrough. The ends of the member 12 are provided with chamfers 16 as shown.

Figure 3:
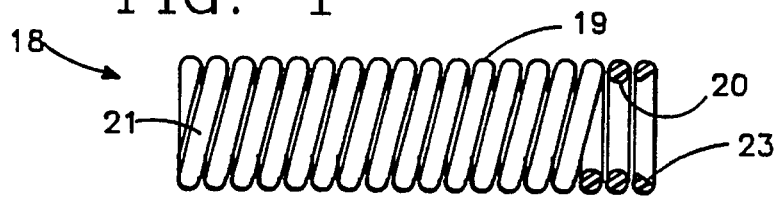
FIG. 3 is a side elevational view partially in cross section of another embodiment of a stent incorporating the present invention.

It should be appreciated that although the cylindrical wall 13 has been shown to be continuous it can be discontinuous as desired. For example, it can be in the form of a helix as shown in FIG. 3 in which the stent 18 in the form of a cylindrical member 19 is formed by turns or loops 21 with a lumen 20 extending therethrough and with chamfers 23 provided at opposite ends. It should be appreciated that other constructions, if desired, can be utilized, as for example one having a perforated wall with openings or holes of various sizes therein.

The member 12 is formed of a plastic material and has a predetermined diameter. The material is of a type which has a built-in elastic memory of a diameter greater than the predetermined diameter. The size, diameter and length of the stent is tailored to the application for which the stent is to be utilized. For example, for cardiovascular applications the stent can have a length ranging from 0.5 cm to approximately 3 cm. It can have a diameter ranging from 0.50 mm to 4.0 mm with a wall thickness ranging from 0.05 to 0.5 mm. In order to facilitate its introduction into a vessel, the diameter of the stent is reduced by a suitable amount, as for example 10 to 30 percent. However, it should be appreciated that, if desired, the reduction can be sufficiently great so that when the stent returns to its original expanded state it could have expanded by 400 to 500 percent from its predetermined diameter.

In accordance with the present invention, in order to have the stent expand to a diameter greater than the predetermined diameter, the stent is provided with a built-in elastic memory. This built-in elastic memory is achieved by utilizing a plastic such as a polymer that has a molecular transition incorporated in the same. The polymeric material is biocompatible. The polymeric material is compounded in such a manner so that the achieved built-in memory can be activated upon subjecting the stent to certain factors as hereinafter explained, which may include adsorption of heat by the plastic, adsorption of liquid by the plastic and a change in the pH in the liquid in which the plastic is disposed. In order to make it responsive to the adsorption of a liquid, it is desirable that the polymeric material possess a range of hydrophilicities ranging from 0 to 50 percent and preferably from 0 to 30 percent. The molecular transitions which can be incorporated in the stent can be in the form of thermal transitions, as for example a crystal melting point between −50° C. and +100° C. of the polymer main chain, and a melting point of between −50° C. and +100° C. of a side chain of the polymer capable of crystallizing, a glass transition temperature between −50° C. and +100° C. and a liquid-crystal phase (mesophase) temperature transition between −50° C. and +100° C. The molecular transitions can also include a local mode molecular transition also accessed by heat.

In accordance with the present invention, various formulations can be utilized for preparing a polymeric materials which can be utilized for achieving built-in elastic memories in stents of the present invention. The types of formulations which can be used are set forth in the examples below.

EXAMPLE 1

Glass Transition Formulation Using a UV Initiator

| | |
|---|---|
| Methyl methacrylate | 4.5 grams |
| Polyethyleneglycol methacrylate | 3.2 grams |
| Butyl methacrylate | 2.0 grams |
| Hexanedioldimethacrylate | 0.3 gram |
| Benzoin methyl ether | 0.03 gram |

All monomers are mixed and then introduced into a transparent spinning tube in a sufficient quantity to provide a desired length of tube with a desired wall thickness. The benzoin methyl ether is a UV initiator. While spinning the tube, an ultraviolet light source is turned on to direct ultraviolet light onto the spinning tube to initiate polymerization. It can be appreciated that the wall thickness of the tube is determined by the amount of monomers placed in the tube as well as the rate of spin of the tube. After the tube has been cured it is removed. It is then raised to a temperature of approximately 37° C., which is slightly above the glass transition temperature for the mixture of Example 1. Assuming that the tube had a original diameter of 3 mm, the tube is stretched to reduce the final outside diameter of the tube to 1 mm. As soon as the desired predetermined diameter has been reached, the temperature of the stent is lowered to a suitable lower temperature, as for example 23° C., while holding the tube in the stretched condition to provide a tube which has a predetermined outside diameter. The appropriate length is cut from the tube and the ends are ground to provide the chamfers 16 on the ends as shown on FIG. 1. The stent is then ready to be positioned in a vessel of a patient in a manner hereinafter described. The stent is then raised to the transition temperature of 37° C. in a manner hereinafter described which causes the stent to attempt to assume the original or greater diameter in its memory, in other words to recover its original condition.

The tube hereinbefore described is manufactured in what can be considered to be a batch process. It is desired to manufacture the tube in a continuous manner. This can be accomplished by polymerizing the monomers into a polymer, pelleting the polymer and feeding the polymer, the crosslinking agent and the UV initiator through a conventional extruder to provide a continuous length of tubing which can be subjected to ultraviolet light to crosslink the extruded tube. The tube can be then be cut into suitable lengths to provide the stents in which the ends are ground and then the stent stretched at the temperature slightly above the glass transition temperature to decrease the diameter to an appropriate diameter, as for example the outside diameter of 1 mm hereinbefore described. The stent can thereafter be utilized in the same manner as the stent which is formed from the liquid monomers.

EXAMPLE 2

Glass Transition Formulation Polymerized by a Thermal Initiator

| | |
|---|---|
| Isobornyl methacrylate | 3.5 grams |
| Hexafluorobutyl methacrylate | 2.6 grams |
| Dodecyl methacrylate | 3.5 grams |
| Butanediol dimethacrylate | 0.04 gram |
| 2,2,Azobis(2-methyl propionitrile)(AIBN) | 0.004 gram |

The first four monomers listed can be mixed and degassed with nitrogen, after which the last ingredient, a thermal initiator, is introduced into the mixture, the mixture being introduced into the spinning tube as hereinbefore described and raising the spinning tube with the material therein to a suitable temperature such as for example 65° C. After polymerization, the tube is cut into suitable lengths to form stents which have their ends ground. The stents are then stretched at an elevated temperature as for example 40° C., and held in that stretched state until they have been cooled to approximately 20° C. By way of example, the pre-stretched outside diameter can be 5.0 mm, whereas the stretched diameter can be reduced to an outside diameter of 3.0 mm. Thereafter, the stent can recover to its original or a larger diameter by heating the same to above the glass transition temperature to 40° C.

EXAMPLE 3

Glass Transition Formulation Polymerized by a Thermal Initiator

| Isobornyl methacrylate | 5.0 grams |
|---|---|
| Octadecyl methacrylate | 2.0 grams |
| Hexyl methacrylate | 2.7 grams |
| Butanediol dimethacrylate | 0.25 gram |
| USP 245(R) | 0.003 gram |

The above-identified monomers were intermixed with the fifth ingredient, a thermal initiator, polymerized by raising the mixture to a suitable temperature as for example 85° C. Tubular stents were then formed in the manner as hereinbefore described. The stent was then stretched at 32° C., which is slightly above the glass transition temperature of the formulation. While in the stretched condition, the temperature was lowered to 20° C. The stent will recover to its original dimensions by immersing the same in water at a temperature of 37° C. Because of this relatively low glass transition temperature, it is necessary that the stent be kept in a cool state prior to insertion of the same into a vessel. In the embodiments hereinbefore described, they were stable at room temperature.

EXAMPLE 4

Glass Transition Formulation Polymerized by a UV Initiator

| Methyl methacrylate | 0.45 gram |
|---|---|
| Polyethyleneglycol methacrylate | 0.34 gram |
| Butyl acrylate | 0.20 gram |
| Ethylene glycol dimethacrylate | 0.01 gram |
| Durocure 1173(R) | 0.002 gram |

The above ingredients were polymerized and formed into a cylindrical tube which was cut into stents. The ends of the stent were ground as hereinbefore described and then the stent was stretched at 25° C. which is approximately 38° C. above its glass transition temperature. The stent was then cooled to a −25° C. while in the stretched state. The stent remains in the stretched state as long as its temperature is maintained below the glass transition temperature of −10° C. To recover the stent to its original dimensions, or for example the larger diameter, the stent is allowed to warm up to ambient temperature. Because of the low glass transition temperature for this stent, the stent must be refrigerated until it is ready for use.

EXAMPLE 5

Glass Transition Formulation Polymerized by a UV Initiator

| Methyl methacrylate | 0.45 gram |
|---|---|
| Polyethyleneglycol methacrylate | 0.35 gram |
| Isobutyl methacrylate | 0.20 gram |
| Hexanediol dimethacrylate | 0.01 gram |
| Durocure 1173(R) | 0.002 gram |

The mixture of the above-identified monomers were polymerized by ultraviolet radiation. The prepared stent was stretched at 30° C., approximately 5° above the glass transition temperature. While retained in the stretched condition, the temperature of the stent was lowered to 15° C. Such a stent recovers its original dimensions when the temperature rises to 27° C.

EXAMPLE 6

Glass Transition Formulation Polymerized by a Thermal Initiator

| Methyl methacrylate | 0.58 gram |
|---|---|
| Polyethyleneglycol | 0.34 gram |
| Butyl methacrylate | 0.54 gram |
| Hexanedioldimethacrylate | 0.02 gram |
| Benzoin methyl ether | 0.002 gram |

The above-identified mixture was polymerized by ultraviolet radiation to form a cylindrical tube. The tube was cut into stents which were fabricated in the manner hereinbefore described. The stent was stretched at 28° C., slightly above the glass transition temperature to reduce the diameter by a factor of 2. While the stent was held in a stretched condition, the temperature was reduced to 20° C. Because of the low glass transition temperature, the stent was stored at 20° C. until it was ready for use at which time it would recover to its initial diameter with an increase in temperature to the glass transition temperature of approximately 28° C.

EXAMPLE 7

Main Chain Crystallizable Formulation

| Polyoctenylene (Vestenamer(R) Huls Corp.) | 70 grams |
|---|---|
| Polyethylene glycol | 25 grams |
| Triallyl isocyanurate | 5 grams |

The above-identified polymers and the crosslinking agent (triallyl isocyanurate) were blended prior and then introduced into an extruder. The extruder served to intimately blend the polymers and the crosslinking agent and to form a cylindrical tube therefrom. If desired, a rectangular strip can be extruded instead of a cylindrical tube.

To achieve crosslinking in the tube or strip, the tube or strip are irradiated with a 2.5 Mrad electron beam irradiation. The irradiated tube is then stretched at 50° C., which is above the melting point of the polymer formulation. The tube is held in this stretched state while the temperature is lowered to 25° C. This formulation provides a melting point of the main chain. The stent recovers to its prestretched dimensions or a greater diameter by immersing the stent in a normal saline solution at 52° C., the melting point of the main chain.

In a similar manner, the rectangular strip was extruded in the same manner and was heated to a temperature of 50° C. and then wound around a mandril to form a helix or coil approximately 4 mm in outside diameter. While in the coiled configuration, the temperature of the strip was lowered to ambient. The coiled stent was irradiated with 5 Mrads of gamma radiation. After radiation, the stent was stretched to reduce its diameter to 2 mm. While in the stretched state, its temperature was lowered to 25° C. The stretched end recoils to its prestretched dimensions by immersing the coil in a normal saline solution at 50° C.

EXAMPLE 8

Side Chain Crystallizable Formulation

| | |
|---|---|
| Methyl methacrylate | 2.0 grams |
| Octadecyl methacrylate | 6.0 grams |
| Isobutyl methacrylate | 2.3 grams |
| Triethylene glycol dimethacrylate | 0.1 gram |
| Perkadox 16(R) | 0.04 gram |

The above-identified monomers were mixed and polymerized at 75° C. in the form of a cylindrical tube. Stents were formed therefrom and stretched from an initial diameter of 2.0 mm to 0.75 mm at 40° C., which is above the melting point of the Octadecyl side chains. While in the stretched state, the stent is cooled to 23° C. Such a stent will recover to its initial dimensions by exposing it to a temperature of 38° C.

EXAMPLE 9

Glass Transition Formulation Recovered by Adsorption of a Liquid

| | |
|---|---|
| Methyl methacrylate | 3.0 grams |
| Hydroxyethyl methacrylate | 4.0 grams |
| Butyl methacrylate | 2.8 grams |
| Polyethylene glycol dimethacrylate | 0.04 gram |
| Durocure 1173(R) | 0.0025 gram |

The above-identified monomers with the UV initiator are mixed and then polymerized by ultraviolet radiation, then formed into a cylindrical stent. The stent was stretched at 34° C. above the glass transition temperature of 25°–27° C. and then cooled in the stretched state to ambient. The stent recovered to its original dimensions by placing it in water at 28° C. The stent adsorbed approximately 10 percent water by weight. By the adsorption of water, the glass transition temperature of the formulation is lowered to initiate recovery of the stent to its original dimensions.

EXAMPLE 10

Glass Transition Formulation Recovered by Adsorption of a Liquid

| | |
|---|---|
| Isobornyl methacrylate | 0.3 gram |
| N-vinyl pyrrolidone | 0.2 gram |
| Butyl acrylate | 0.45 gram |
| Polyethylene glycol dimethacrylate | 0.05 gram |
| Benzoyl peroxide | 0.004 gram |

The above-identified monomers were mixed and polymerized with an ultraviolet source to form a tubular stent. The stent was stretched at 32° C. and cooled to ambient in the stretched state. The stent later recovers to its prestretched dimensions by placing the stretched stent in a normal saline solution at 30° C. The stent adsorbs approximately 15 percent water by weight. In so doing, the glass transition temperature of the stent was lowered below the temperature of the saline solution initiating recovery of the stent to its original dimensions.

EXAMPLE 11

Recovery by a Change in the pH of the Stent

| | |
|---|---|
| Methyl methacrylate | 0.35 gram |
| Methacrylic acid | 0.15 gram |
| Hexadecyl methacrylate | 0.45 gram |
| Polyethylene glycol dimethacrylate | 0.05 gram |
| USP 245(R) | 0.004 gram |

The above-identified monomers were intermixed and polymerized by the use of heat at 80° C. to form a tubular stent. The stent was stretched to reduce its diameter from 3 mm to 2 mm at 35° C. The temperature was then reduced to ambient while the stent was in the stretched state. Such a stent recovers its original dimensions by placing the same in a carbonate buffer solution whose pH was 8.4. This was accomplished because the polymer contained acid groups and was subjected to a basic bath to achieve their recovery.

EXAMPLE 12

Recovery by a Change in the pH of the Stent

| | |
|---|---|
| Isobornyl methacrylate | 0.2 gram |
| Acrylic acid | 0.2 gram |
| Octadecyl methacrylate | 0.35 gram |
| Polyethylene glycol dimethacrylate | 0.1 gram |
| Perkadox 16(R) | 0.03 gram |
| N-vinyl pyrrolidone | 0.15 gram |

The above-identified ingredients were mixed together to provide a formulation which was polymerized at a temperature of 70° C. The stent was then stretched at 50° C. to reduce its diameter from 5.0 mm to 2.5 mm. While in the stretched state the temperature of the stent was lowered to ambient. Such a stent recovers to its original condition when placed in an aqueous buffer solution having a pH of 8.5.

EXAMPLE 13

Liquid Crystal

| | |
|---|---|
| Para cyclohexyl methacrylate | 0.8 gram |
| Octadecyl methacrylate | 0.1 gram |
| Hexanedioldimethacrylate | 0.1 gram |
| Durocure 1173(R) | 0.03 gram |

The above monomers with the UV initiator are mixed and polymerized by UV radiation, then formed into a cylindrical stent. The stent was stretched at 63° C., the liquid crystal transition temperature. While in the stretched state the temperature was lowered to ambient. Subsequent recovery of the stent to its original dimensions were accomplished by raising the temperature of the stretched stent above 63° C.

From the above examples it can be seen that to impart a memory to the stent, the stent is stretched at a temperature at or above one of the transition identified above. Then while being held in the stretched state, the temperature of the stent is lowered to a temperature below the stretching temperature. Later when the stent is maintained at temperatures below the transition temperature, the stent will remain in a stretched state.

Figure 4:
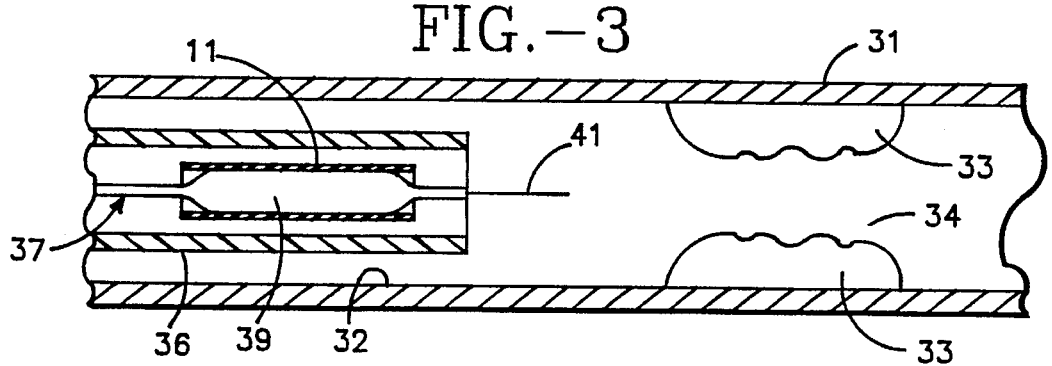
FIG. 4 is a cross sectional view of a vessel showing the delivery apparatus for delivering a stent of the type shown in FIG. 1 into a stenosis into the vessel.
Figure 5:
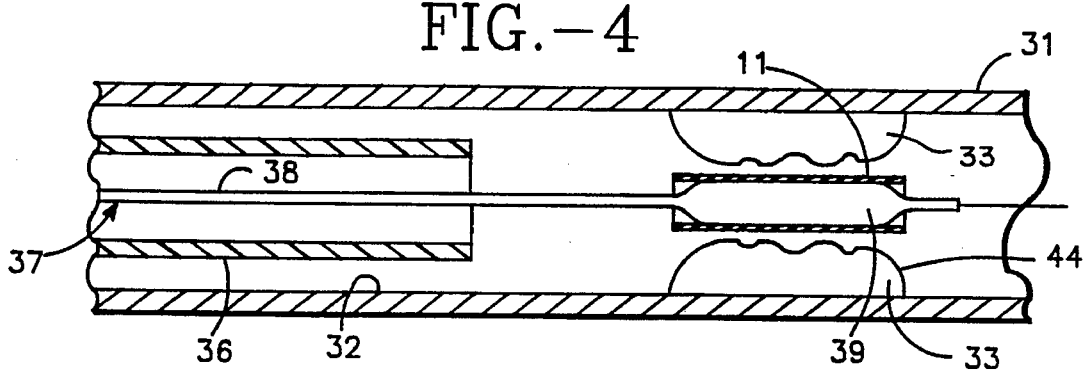
FIG. 5 is a cross sectional view similar to FIG. 4, but showing the stent delivered into the stenosis in the vessel.

The stent of the present invention can be delivered to a site in a vessel in a body of a patient while it is in the stretched state. This can be accomplished in any suitable manner. For example, as shown in FIG. 4, vessel 31 as shown, for example, can be an arterial vessel in the heart which is provided with a flow passage therein. Let it be assumed that a stenosis 33 has developed in the vessel, and that this stenosis has been reduced by a conventional angioplasty procedure by using an inflated balloon to compress the plaque forming the stenosis to provide enlarged flow passage 34 through the stenosis. Let is also be assumed that it is desirable to place a stent of the present invention in the flow passage 34 of the stenosis 33 to prevent the stenosis 33 to again grow and appear to close off the passage 34. Let it be assumed that a guiding catheter 36 of a conventional type has been introduced into the patient through the femoral artery and advanced into a position adjacent to the stenosis 33. A balloon catheter 37 of a conventional type is utilized. As is well known to those skilled in the art, the balloon catheter is provided with a flexible elongated element 38 which has a balloon inflation lumen (not shown) disposed therein which is in communication with a balloon 39 mounted on the distal extremity of the flexible elongated element 38. The balloon catheter 37 is also provided with a guide wire 41 which can be of a fixed type or a movable guide wire of types well known to those skilled in the art. With the balloon catheter outside of the patient's body, the balloon 39 is deflated and a stent 11 of the type hereinbefore described is slid over the deflated balloon 39 so that it is frictionally engaged by the balloon. The balloon catheter with the stent 11 thereon is then introduced into the guiding catheter which has already been positioned in the patient's body for the angioplasty procedure. The balloon catheter is advanced in the conventional manner so that it is advanced into the stenosis 33. Radiopaque elements (not shown) typically are carried by the balloon catheter in the vicinity of the balloon to facilitate locating the lumen of the balloon catheter as it is advanced in the vessel 31 of the patient. The guide wire 41 is advanced into the flow passage 34, followed by the balloon catheter by advancing the balloon with the stent 11 into the passage 34 so that it is lodged within the stenosis 33 as shown in FIG. 5.

Figure 6:
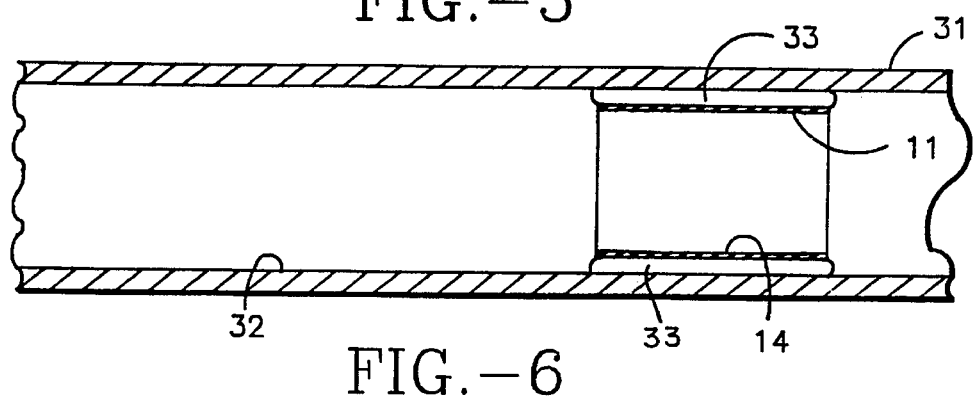
FIG. 6 is a cross sectional view similar to that shown in FIG. 5 showing the stent in an expanded condition within the stenosis and with the deliver apparatus removed from the vessel.

Let it be assumed that the stent 11 is one of the type made in accordance Example 1, and that after it has been positioned as shown in FIG. 4 within the stenosis 33 it is desired to subject the stent 11 to heat in order to cause the stent to assume its recovery diameter, or in other words, the greater diameter in its memory. It can be supplied to the stent by introducing a gas or liquid, preferably a liquid because of its greater heat transfer capabilities, to the balloon inflation lumen in the flexible element 38 and introducing the same into the balloon 39 to inflate the balloon. The heated liquid in the balloon will cause heat to be rapidly transferred to the stent 11 to raise the temperature of the stent until the temperature reaches the glass transition temperature allowing the stent to return to its recovery diameter. This recovery is facilitated by the expansion of the balloon 33 which applies outwardly extending forces to the internal diameter of the stent 11. It should be appreciated that in the event it is desired to stop the flow of a liquid such as blood through the passage 34, that the balloon 39 can be deflated after it has been inflated for a sufficient length of time as for example 2–3 seconds, and thereafter again reinflated until the stent 11 has expanded to firmly engage the stenosis 33 so that it will be frictionally retained therein. The balloon 39 is then deflated, after which the balloon catheter 37 can be removed followed by removal of the guiding catheter 36, so that thereafter all than remains is the stent 11 firmly positioned within the stenosis 33 as shown in FIG. 6 with the flow passage in the stent 11 being opened to the flow passage 32 and permitting a liquid such as blood flowing in the vessel to pass through the stenosis by passing through the passageway 14.

Stents made in accordance with the other examples hereinbefore described can be positioned in a stenosis in the same manner by the use of a balloon catheter, and then permitting the stent to assume its recovery diameter by increasing the temperature of the stent, after it has been positioned in the stenosis, above the stretched temperature as hereinbefore described. As hereinbefore explained, the recovery diameter can be achieved by permitting the stent to adsorb water from a body fluid as for example from the blood in an artery. The stent can also assume its recovery diameter by being subjected to the pH level of the liquid in which the stent is disposed. It is also explained, that the return to the recovery diameter can be aided by outward pressures of the balloon being applied internally of the stent.

For stents which are stretched at or below the body temperature, it is necessary to keep the temperature of the stent below the body temperature prior to insertion of the stent into the vessel of the patient to prevent premature recovery. Once the stent has been positioned in the stenosis in the vessel, the stent is exposed to body temperature by coming into contact with body fluids which will cause the stent to spontaneously recover to its pre-stretched dimensions.

For stents which have been stretched at temperatures above the body temperature, heat from an external source is applied to the stent to raise its temperature to the stretched temperature permitting it to recover its pre-stretched dimensions. As hereinbefore explained, such external heat can be applied by using a heated liquid for inflating and deflating the balloon on the balloon catheter. Alternatively, infrared, microwave or radiofrequency sources as well as resistive heating can be utilized for supplying such external heat to the stent.

For stents which have been stretched at temperatures below the body temperature, the stent should be maintained at a temperature below the body temperature, as for example it can be refrigerated. When it is desired to utilize the stent, the stent can be placed on the balloon catheter and placed within the guiding catheter. The insulating properties of the guiding catheter can be utilized to protect the stent from the body temperature. Alternatively, the guiding catheter can be provided with a fluid which is below the stretched temperature of the stent. Also, the temperature of the stent can be reduced to a low value by refrigeration so that prior to insertion into the vessel its temperature is substantially less than the temperature of the vessel, making it possible to deploy the stent into the stenosis prior to the time that the temperature has reached the stretched temperature. Thereafter, the stents continued contact with liquids at the body temperature will initiate recovery of the stent to its original dimensions.

In order to enhance ingrowth of intimal and endothelial vessel tissue into the stent, the stent can be made of a porous material to enhance compatibility of the stent with the vessel. Examples of such stents are set forth below.

EXAMPLE 14

Microporous Stent

| | |
|---|---|
| Methyl methacrylate | 0.38 gram |
| Polyethylene glycol methacrylate | 0.28 gram |
| Isobutyl methacrylate | 0.20 gram |
| Hexanedioldimethacrylate | 0.03 gram |
| Benzoin methyl ether | 0.003 gram |
| Polyethylene glycol | 0.11 gram |

The above-identified ingredients were thoroughly mixed and then polymerized by the use of ultraviolet radiation to provide a cylindrical stent in the manner hereinbefore described. The stent is immersed in water at 60° C. The water is stirred around the stent. The heated water causes the polyethylene glycol dispersed within the matrix of the stent to be dissolved out of the stent leaving voids and/or pores within the wall of the stent. Typically, the polyethylene glycol will be dissolved out in approximately 120 minutes at that temperature. The stent is then dried and then elevated to a temperature of approximately 55° C. The stent is then stretched to achieve the desired predetermined diameter in the stent. After the predetermined diameter has been reached and while the stent is maintained in a stretched state, the temperature is lowered to ambient. The recovery dimensions of the stent can be initiated by elevating the temperature of the stent to 60° C. or greater.

Such a stent, because of its porosity, promotes ingrowth of intimal and endothelial vessel tissue into the pores of the stent.

EXAMPLE 15

Microporous Stent

| | |
|---|---|
| Isobornyl methacrylate | 0.3 gram |
| Hexyl methacrylate | 0.2 gram |
| Hydroxyethyl methacrylate | 0.25 gram |
| Ethylene glycol dimethacrylate | 0.02 gram |
| Polyvinyl pyrrolidone | 0.25 gram |
| AIBN | 0.004 gram |

The above-identified ingredients were polymerized at 75° C. to again form a cylindrical stent in the manner hereinbefore described. The stent is then immersed in water at the ambient temperature in an ultrasonic bath. The polyvinyl pyrrolidone which was dispersed within the polymer matrix is dissolved out of the stent leaving microscopic pores or voids within the wall of the stent. After drying, the stent is stretched after being elevated to a temperature of approximately 42° C. While being held in the stretched state, the temperature was lowered to ambient. Such a stent recovers its original dimensions when subjected to a temperature of 45° C.

The porosity of the wall of the stent again permits the ingrowth of intimal endothelial tissue to enhance compatibility of the stent with the vessel.

Thus it can be seen that stents of the present invention can be formed so as to enhance the ingrowth of intimal endothelial tissue which helps to ensure that the stent will remain in the desired location within the vessel and will not move about in the vessel. Such endothelial vessel tissue growth should occur within approximately four weeks after insertion into the vessel.

In addition, stents of the present invention can be formulated so as to be able to carry a medical agent such as thrombolytic agents, growth factors and slow-release medications. Also, controlled release drug administration can be provided by utilizing the stent as an inert polymeric drug carrier. For example, the drug may be incorporated in a controlled release system as a dispersion in a matrix. The matrix can be formed with a dispersion of uniform drug particles in the biocompatible polymeric materials of the type hereinbefore described in connection with the stent of the present invention. Such stents also can be caused to incorporate the medical agents by causing the stent to imbibe the medical agent such as by exposing the same to a fluid or a liquid carrying the medical agent.

From the foregoing it can be seen that there has been provided a stent incorporating the present invention and a apparatus and method for use therewith which has numerous advantages. It has low protein adsorption and is thus biocompatible. It can be provided with a desired hydrophilicity to improve its compatibility with the vessel. The stent can be made with a desired stiffness so as to match the compliance of the vessel. Because of its built-in memory, the stent need not be physically constrained prior to use to prevent premature recovery. The stents can be made porous to facilitate the ingrowth of intimal and endothelial cells. The stents can be formulated and/or treated so as to carry medical agents which remain with the stent.

In general, the polymer compositions can be containing one or more of the following: acrylic acid, methacrylic acid, esters of acrylic acid and methacrylic acid and combinations thereof. Such compositions can also be provided which contain acrylic acid, methacrylic acid, esters of acrylic acid and methacrylic acid with N-vinyl pyrrolidone. Compositions can also be provided containing copolymers of ethylene oxide and vinyl monomers and other compositions which contain acrylamide esters. Other compositions can contain acrylic acid, methacrylic acid, acrylic esters, methacrylic esters, vinyl pyrrolidone and acrylamide esters. These compositions can contain copolymers of vinyl pyrrolidone and monomers such as

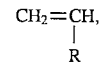

and alternatively copolymers of vinyl ether and monomers such as

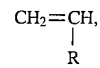

where $R=C_nH_{(2n+1)}$, and alternatively copolymers of maleic anhydride. Compositions also can be provided containing blends of polymers such as polyethylene oxide, Vestenimer® (polyoctenylene), polyethylene, polysiloxanes, nylons and polyesters. Other compositions can contain polymers and plasticizers which depress the glass transition temperature within the temperature range of −50° C. to +100° C.

What is claimed is:

1. A self-restrained stent for use in the lumen defined by a wall of a vessel having a lumen therein of a patient, comprising a hollow substantially cylindrical member formed of a polymeric composition having an initial predetermined size which is less than the inside diameter of the lumen of the vessel so that the substantially cylindrical member can be inserted into the lumen of the vessel, said polymer composition forming said substantially cylindrical member having a transition characteristic therein whereby when the transition characteristic is activated the substantially cylindrical member will change its dimensions in all directions and assume a greater diameter than the initial predetermined diameter and come into engagement with the wall of the vessel to form a flow passage in the lumen of the vessel.

2. A stent as in claim 1 for use with a liquid wherein said transition characteristic is activated by the adsorption of heat by the polymeric composition.

3. A stent as in claim 1 for use with a liquid wherein the transition characteristic is activated by the adsorption of the liquid by the polymeric composition.

4. A stent as in claim 1 for use with a liquid having a change in pH wherein the transition characteristic is activated by the change in the pH of the liquid in which the polymeric composition is disposed.

5. A stent as in claim 1 wherein said polymeric composition is porous to facilitate the ingrowth of neointimal and endothelial vessel tissues.

6. A stent as in claim 1 together with a medical agent carried by the stent.

7. In the combination of a balloon catheter and a stent, a balloon catheter having a distal extremity with a balloon mounted thereon, the balloon catheter including a balloon inflation lumen for inflating and deflating the balloon, the balloon being in a deflated condition and a stent mounted over the deflated balloon and frictionally engaging the deflated balloon, the stent being characterized in that it is substantially cylindrical and self restrained with a predetermined diameter, said stent being formed of a biocompatible polymeric composition having a transition characteristic therein, whereby when the transition characteristic is activated the stent will change its dimensions in all directions and will attempt to assume a greater diameter than the predetermined diameter.

8. An apparatus as in claim 7 wherein said polymeric composition is porous.

9. An apparatus as in claim 7 together with means for introducing a heated liquid into the balloon for inflating the balloon and for transferring heat to the stent to activate the transition characteristic of the stent.

10. A self-restrained stent for use in a lumen defined by a wall of a vessel having a lumen therein of a patient comprising a hollow substantially cylindrical member formed of a plastic material having an initial built-in elastic predetermined diameter which is less than the diameter of the lumen in the vessel so that the substantially cylindrical member can be inserted into the lumen of the vessel, said plastic material of cylindrical member also having a memory based on a transition provided therein of a diameter greater than the initial built-in elastic predetermined diameter and at least as great as the diameter of the lumen of the vessel, said plastic being characterized in that it will change its dimensions in all directions and will assume the greater diameter in its memory and move into engagement with the wall of the vessel upon the occurrence of one or more of the following conditions selected from the group consisting of: (a) adsorption of heat by the plastic material; (b) adsorption of a liquid by the plastic material; and (c) a change in the pH in the liquid in which the plastic member is disposed.

* * * * *